United States Patent [19]

Adams

[11] Patent Number: 4,542,103

[45] Date of Patent: Sep. 17, 1985

[54] LATEX AGGLUTINATION DETERMINATION OF IGG IN NEONATALS AND IN COLOSTRUM

[75] Inventor: Ernest C. Adams, Elkhart, Ind.

[73] Assignee: Miles Laboratories, Inc., Elkhart, Ind.

[21] Appl. No.: 552,482

[22] Filed: Nov. 16, 1983

Related U.S. Application Data

[63] Continuation-in-part of Ser. No. 519,500, Aug. 2, 1983, abandoned, which is a continuation of Ser. No. 417,661, Sep. 13, 1982, abandoned.

[51] Int. Cl.$^4$ .............................................. G01N 33/54
[52] U.S. Cl. ..................................... 436/534; 436/533
[58] Field of Search ................................ 436/533, 534

[56] References Cited

U.S. PATENT DOCUMENTS

| | | | |
|---|---|---|---|
| 3,873,683 | 3/1975 | Fishbein | 436/534 |
| 3,992,517 | 11/1976 | Lowke | 436/534 X |
| 4,003,988 | 1/1977 | Hoff | 436/534 |

[57] ABSTRACT

A method for determining the amount of IgG present in a neonatal foal or calf or in the colostrum of a dam or cow. The method involves contacting a body fluid sample with biologically inert latex particles, measuring the amount of agglutination which occurs, and determining the amount of IgG present. The latex particles are diluted to a final concentration of from about 0.25 to 2.0 percent (w/v) at a pH of from about 7.5 to 9.0 with a buffer. The body fluid is diluted to a range of from 0.01:5 parts to 0.01:2160 parts, v/v basis, at a pH of from about 7.5 to 9.0.

6 Claims, No Drawings

LATEX AGGLUTINATION DETERMINATION OF IGG IN NEONATALS AND IN COLOSTRUM

BACKGROUND OF THE INVENTION

This is a continuation-in-part of application Ser. No. 519,500, filed Aug. 2, 1983, now abandoned, which was a continuation of application Ser. No. 417,661, filed Sept. 13, 1982, now abandoned.

Neonatal humans and other species obtain immunoglobulins, i.e., antibodies, across the placental barrier prior to birth. The presence of such immunoglobulins especially provides sufficient antibody levels in the newborn to provide resistance to infectious diseases. One type of immunoglobulin, IgG, appears very early after an immunogenic stimulus and along with its major intravascular distribution, may enable IgG to serve as a first line of defense.

In contrast, foals or calves receive virtually no IgG across the placental barrier and at birth have extremely low levels of IgG, designated as hypogammaglobulinemia. This situation usually is reversed following the ingestion of IgG rich colostrum and its absorption by the intestinal epithelium. IgG must be absorbed by nursing in approximately 24 hours after birth; after this period IgG is no longer absorbed in the intestine.

Absorption of colostrum IgG is essential for the good health of the foal or calf in the neonatal period. Failure to absorb proper amounts of IgG is the most important factor predisposing otherwise normal foals to infection and death. [See *J. Am. Vet. Med. Ass.*, 166:71 (1975)].

Failure to transfer IgG should be diagnosed accurately and quickly so that a decision can be made whether to administer therapy or to dispose of the animal. Therapy can include injection of IgG.

DESCRIPTION OF THE PRIOR ART

Numerous prior art articles disclose a test for immunoglobulin utilizing a "latex flocculation test", e.g., flocculating polystyrene latex particles. The test generally involves coating latex particles with an antigenic substance, e.g., hormones, or blood proteins such as albumin or immunoglobulins such as IgG and IgM. Latex particles are negatively charged and the protein binds by means of an adsorption phenomena. A second step involves adding a second reagent which can cause agglutination of the coated latex particles.

*Aust. Vet. J.*, 56:513 (1980) describes a test for detecting absorption of colostrum immunoglobulins in neonatal foals. The test procedure involved mixing together latex particles and anti-serum to purified horse immunoglobulin to coat the latex particles with anti-horse IgG antibodies. After incubation, the coated latex particles were washed free of unadsorbed anti-horse IgG with fresh buffer and reconstituted with buffer. The antibody-latex mixture was then added to test samples of foal plasma. Development of a gritty, white agglutination pattern indicated a positive test for the presence of immunoglobulin.

*Am. J. Med.*, 21:888–893 (1956) describes application of the latex flocculation test to the serologic diagnosis of rheumatoid arthritis, utilizing an IgM immunoglobulin known as rheumatoid factor (RF). The test procedure involved first coating latex particles with human gamma globulin. After incubation the coated latex particles were washed free of unadsorbed gamma globulin with fresh buffer and reconstituted with buffer. The gamma globulin-latex mixture was then added to a serum sample from a patient with rheumatoid arthritis. Agglutination occurred in 71 percent of the patients with arthritis. When the test was modified by mixing a latex particle suspension and the serum, without gamma globulin, only 11 percent of rheumatoid serums caused agglutination.

U.S. Pat. No. 3,088,875 describes a latex flocculation test for a "C-reactive" protein commonly found in the serum of patients with active inflammatory or tissue-destroying disease. The test involved mixing the latex particles with human gamma globulin and heating at 57° C. The antibody-coated latex particles were then mixed with diluted serum from a patient. Agglutination indicated the presence of the C-reactive protein.

U.S. Pat. No. 3,551,555 describes a test which can be used to detect an antigen such as human chorionic gonadotropin, in which latex particles are first coated with an inert protein such as albumin or lactalbumin and subsequently coated with either an antigen or antibody. The protein-antibody or protein-antigen coated latex particles were then mixed with diluted serum from a patient. Agglutination indicated the presence of an antigen.

Each of the references described above involve first coating the latex particles with a proteinaceous material and then reacting the coated latex particles with a second reagent, wherein the second reagent in effect forms inter latex cross bridges which in turn cause "bridge" agglutination. None of the references suggest or disclose that the level of foal or calf IgG or the level of IgG in colostrum from a dam or cow can be determined without the use of an antibody-antigen reaction.

SUMMARY OF THE INVENTION

The present invention relates to a method for detecting the level of IgG in neonatal foals or calves or in the colostrum of a dam or cow. The method involves the steps of contacting a body fluid sample with biologically inert latex particles, measuring the amount of agglutination which occurs and determining the amount of IgG present in the sample. The latex particles are diluted to a final concentration of from about 0.25 to 2.0 percent (w/v), at a pH of from about 7.5 to 9.0, with a buffer. The body fluid is diluted to a range of from 0.01:5 parts to 0.01:2160 parts, v/v basis, at a pH of from about 7.5 to 9.0.

DETAILED DESCRIPTION OF THE INVENTION

The critical levels of IgG appear to be: below 200 mg/dl indicates need for therapy; between 200 and 400 mg/dl is questionable; and above 400 mg/dl is sufficient. The claimed method provides a convenient measurement of these levels.

The latex particles used in the present invention can be any suitable biologically inert particles. Suitable particles include polyvinyl toluene, styrene-butadiene latex, styrene-divinyl benzene latex, acrylic latex and polystyrene latex. The latex particles can be from 0.109 to 0.81 microns in size. Latex particles are commercially available from Dow Chemical Company, Midland, Mich.; Monsanto and Company, St. Louis, Mo.; Rhone-poulenc, Paris, France and AB Bofors, Örebro, Sweden.

The latex particles are commercially available as a suspension, e.g., a 10 percent aqueous (w/v) latex solution and can be diluted with a suitable buffer. Suitable buffers are those which are sufficiently soluble in water and possess a high buffering capacity at a pH of about 7.5 to 9. For example, borate-saline, glycine-saline and N,N-bis-2-hydroxyethyl-glycine, are suitable buffers.

A suitable borate buffer can be prepred from 12.2 mmoles $Na_2B_4O_7$ and 7.1 mm of HCl per cc. A saline solution of from 0.08 percent to 10 percent (w/v) can be added to the borate. A preferred range is from 0.3 to 1.25 weight percent. Optionally the borate-saline buffer can be prepared from 50 cc of 0.1M boric acid and 5.9 ml of 0.1N NaOH made up to 100 cc with water and the pH adjusted to about 8.2; 0.85 gm of NaCl is added to each 100 ml of buffer.

A suitable glycine-saline buffer is 0.1M, pH 8.2 containing 10 g NaCl per liter. The latex particles are diluted to a final concentration of from 0.25 to 2 percent (w/v), at a pH of from about 7.5 to 9.0.

The body fluid can be blood plasma, serum or whole blood from a neonatal foal or calf, or can be colostrum from a dam or cow. The body fluid is diluted to a range of from 0.1:5 parts to 0.1:2160 parts body fluid:buffer v/v basis, with a buffer as described above.

Experimental tests have indicated the importance of the particle size limitations 0.109 to 0.81 microns. As the latex particle size decreases, the amount of surface area greatly increases, making it difficult to detect agglutination. As the latex particle size increases, the surface area greatly decreases.

Similar considerations involve the 0.25 to 2.0 weight percent limitations on the amount of latex particles present. As the concentration of latex particles increases to greater than 2.0 percent by weight, IgG determination becomes unworkable because of the large amounts of IgG required. As the concentration of latex particles decreases to less than 0.25 percent by weight, it becomes increasingly difficult to detect agglutination.

Using the latex particle sizes and concentration described above, it has been found that the body fluid to be tested can be diluted within the range 0.01:5 parts to 0.01:2160 parts body fluid:buffer (v/v basis). If the body fluid is diluted to greater than 0.01:2160 body fluid:buffer, particles of greater than 1 micron would be required for agglutination within the same IgG level and would be difficult to work with within the system. If the body fluid is more concentrated than 0.01:5 parts body fluid:buffer, any of the described size of latex particles would be agglutinated by insignificant levels of IgG.

The proper dilution of latex and serum with a suitable buffer can be easily determined by one skilled in the art in the manner described hereinafter. A preferred embodiment utilizes latex particles which are 0.190 to 0.250 microns in size diluted to a final concentration of 0.65 to 0.70 percent (w/v). The preferred dilution of body fluid with buffer is from 0.01:8 to 0.01:16 for foal serum.

In the following Examples, unless otherwise indicated, the latex particle solutions were obtained from Dow Chemical Company.

Control Procedure

Foal serum samples were obtained from neonatal foals, about 6 to 8 hours after birth. Radial immunodiffusion test kits (RID), commercially available from Miles Laboratories, Inc., Elkhart, Ind., were used as follows. The kit contains anti-horse IgG incorporated in buffered agarose. The agarose has holes punched in it. A selected standard amount of the serum to be measured was placed in a hole and standard control samples were placed in other holes. The serum and agarose were allowed to incubate at room temperature for about 16 to 24 hours. A ring of precipitation formed around each of the holes, which was proportional to the amount of IgG present. The diameter of each of the rings was measured and plotted against the concentration on semi-log paper. Based on this, the amount of IgG present in the serum samples was determined.

EXAMPLE I

A 10 percent (w/v) solution of polystyrene latex particles, having a particle size of 0.22 microns was diluted 1:5 (v/v) with N,N-bis-2-hydroxyethylglycine buffer (0.2M, pH 8.5) to a final concentration of about 2 percent (w/v).

For each test, duplicate foal serum samples used in the "Control Procedure" were used. It was determined from a series of tests that a convenient IgG determination level would be provided if the amount of serum required was not greater than about 4 to 6 drops. Based on these tests, five μl of foal serum was added to 8 ml N,N-bis-2-hydroxyethylglycine buffer (0.2M, pH 8.5) and mixed well (0.01 part sample:16 parts buffer, v/v).

Each drop of the diluted latex particle mixture was determined to be 0.025 ml; one-half drop of the diluted latex was determined to be about 0.01 ml. Two drops (each 0.025 ml. size) of the diluted latex particle mixture were placed on a glass slide. One drop of foal serum, diluted as described above, was added and stirred. The slide was gently rocked and rotated back and forth, and the mixture observed for agglutination. If there was no clearly visible agglutination after about 10 seconds, a second drop of diluted serum was added and mixed in the same manner. This titration procedure was continued until agglutination occurred. The procedure was repeated for each diluted foal serum sample.

The IgG agglutination test results obtained were compared with the IgG test results obtained in the Control Procedure. Test results obtained are summarized below.

TABLE I

| RID IgG Level | Test Method Amount of Serum Added |
|---|---|
| >400 mg/dl | 1 drop diluted serum/2 drops diluted latex positive agglutination |
| ≧400 mg/dl | 2 drops positive agglutination |
| 200–400 mg/dl | 3 drops positive agglutination |
| ≦200 mg/dl | 4 drops positive agglutination |
| <200 mg/dl | >4 drops positive agglutination |

Using the criteria established in Table I, a series of 77 foal samples was tested by the method of the invention and compared with the IgG levels established by the RID Control Procedure. Test results are summarized below.

TABLE II

Summary of Titration Results
Percentage of Common Results Within Each IgG Level Group

| Group IgG Level (RID) mg/dl | No. Samples in Group | (No.)/Percentage Agglutination Based on Test Procedure | | | | | | | | | |
|---|---|---|---|---|---|---|---|---|---|---|---|
| | | 1 dr | 1.5 dr | 2 dr | 2.5 dr | 3 dr | 3.5 dr | 4 dr | 4.5 dr | 5 dr | 5.5 dr |
| >400 | 52 | (8) 15.3% | (12) 23% | (28) 53.% | (4) 7.7% | 0 | 0 | 0 | 0 | 0 | 0 |
| 200–400 | 16 | 0 | 0 | 0 | (2) 12.5% | (9) 56.3% | (3) 18.3% | (1) 6.25% | (1) 6.25% | 0 | 0 |
| <200 | 9 | 0 | 0 | 0 | 0 | 0 | 0 | (6) 60% | (1) 10% | 0 | (2) 20% |
| TOTAL SAMPLES | 77 | | | | | | | | | | |

Out of a total of 77 samples tested, the IgG level of 73 samples (94.8 percent) were in agreement with the IgG levels obtained in the RID Control Procedure. Similar results were obtained when the accuracy of the test procedure was compared to the ZnSO4 test described in *Eq. Vet.*, 6:109 (1974).

These test results demonstrate that the claimed method for determining IgG level has a high degree of accuracy, when measured against a recognized commercially available test.

At the particular reaction conditions, utilized, i.e., a latex particle size of 0.22 microns diluted to 2.0 percent (w/v) and a body fluid:buffer ratio of 0.01 part:16 parts (v/v), the IgG level was conveniently determined by using up to 4.5 drops of diluted body fluid.

EXAMPLE II

Serum samples were obtained from two foals and determined by RID testing to have an IgG concentration of about 1500 mg/dl and about 0–200 mg/dl, respectively. The samples were mixed to produce a series having the following IgG levels (mg/dl): 750, 500, 375, 300 250 and 166. These serum samples were used as described below.

A 10 percent (w/v) solution of polystyrene latex particles, having a particle size of 0.22 microns was diluted 1:5 (v/v) with a N,N-bis-2-hydroxyethyl-glycine buffer (0.2M, pH 8.5) to a final concentration of about 2 percent (w/v).

For each test, 5 μl of foal serum having the concentration described above was added to 6 ml of the above buffer and mixed well to a final concentration of 0.01 part serum to 12 parts buffer (v/v). One drop of the diluted latex mixture was mixed on a slide with 1 drop of the diluted serum, rocked and rotated and observed for agglutination. If no agglutination occurred, a second diluted latex sample (1 drop) was mixed on a slide with 2 drops of the diluted serum. Again, if no agglutination occurred, the procedure was repeated with 3 drops of diluted serum. Test results obtained are summarized below.

TABLE III

| mg/dl IgG (RID) | Amount of Serum Added |
|---|---|
| 750 × 2 = 1500 | 1 drop positive agglutination |
| 500 × 2 = 1000 | 1 drop positive agglutination |
| 375 × 2 = 750 | 1 drop positive agglutination |
| 300 × 2 = 600 | 1 drop positive agglutination |
| 250 × 2 = 500 | 1 drop negative, 2 drops positive agglutination |
| 166 × 2 = 332 | 1 and 2 drops negative, 3 drops positive agglutination |

The test results obtained in Table III were compared with the titration results of Example I. Because the titration results shown in Table I were obtained by using 1 drop serum/2 drops diluted latex, the concentrations shown in Table III were multiplied by a factor of 2 to compare Table I and Table III.

The results indicate that the procedure of Example II correlates the IgG level with the IgG level obtained from the titration procedure of Example I (correlated to the RID Control Procedure). For example, at a level of 166 mg/dl IgG (×2=332 mg/dl) 3 drops of serum gave a positive agglutiantion; this is within the range 200–400 mg/dl indicated by a 3 drop agglutination shown in Table I. Similar results are indicated for the other IgG levels.

It is clear that in carrying out the process described in Examples I and II that the agglutination of the body fluid and latex can be observed and the level of IgG present in the sample determined therefrom. One skilled in the art can adjust the concentration of buffer and the size and concentration of latex particles required to detect IgG levels in a body fluid. These levels can easily be optimized to produce a convenient IgG test.

In the following Examples, a wide range of reaction conditions was utilized. The reaction conditions were not necessarily optimized; therefore the agglutination values obtained, i.e., the IgG levels, in many of the Examples were not directly comparable with the agglutination values obtained in Example I. However, in each Example, as the amount of IgG present in the samples was increased or decreased, the amount of agglutination varied such that the IgG was measurable by the claimed method.

Unless indicated otherwise, the concentrations of foal serum used in the following Examples were obtained as described in Example II.

In order to determine the effect of changing the particle size to about 0.10 microns, the following procedure was carried out.

EXAMPLE III

A 10 percent aqueous solution of polystyrenebutadiene latex particles, having a particle size of 0.109 microns was diluted 1:15 with the buffer of Example I to a final concentration of about 0.67 percent (w/v).

For each test, 5 μl of foal serum was added to 6 ml of the above buffer and mixed well to a final concentration of 0.01 part serum to 12 parts buffer (v/v). One drop of the diluted latex mixture was mixed with 1, 2, or 3 drops of the diluted serum as described in Example I. Test results obtained are summarized below.

TABLE IV

| mg/dl IgG (RID) | Amount of Serum Added |
|---|---|
| 750 × 2 = 1500 | 1 drop negative, 2 drops positive agglutination |
| 500 × 2 = 1000 | 1 drop negative, 2 drops positive |

TABLE IV-continued

| mg/dl IgG (RID) | Amount of Serum Added |
|---|---|
| | agglutination |
| 375 × 2 = 750 | 1, 2 drops negative, 3 drops positive agglutination |
| 300 × 2 = 600 | 1, 2, 3 drops negative agglutination |

As seen from the above data, as the amount of IgG present in the serum sample decreased, the amount of serum required for agglutionation increased. The decreased latex particle size produced a corresponding increase in the surface area which required a greater dilution of the latex particle concentration.

In Examples IV and V, the foal serum samples were adjusted to produce a series having the IgG concentration shown in the respective Tables.

EXAMPLE IV

A 10 percent aqueous solution of polystyrene latex particles, having a particle size of 0.497 microns was diluted 1:5 with the buffer of Example I to a final concentration of about 2 percent (w/v).

For each test, 5 μl of foal serum was added to 108 ml of the above buffer and mixed well to a final concentration of 0.01 part serum to 216 parts buffer (v/v). One drop of the diluted latex was mixed with 1, 2 or 3 drops of the diluted serum as described in Example I. Test results obtained are summarized below.

TABLE V

| mg/dl IgG (RID) | Amount of Serum Added |
|---|---|
| 900 × 2 = 1800 | 1 drop positive agglutination |
| 370 × 3 = 740 | 1 drop questionable, 2 drops positive agglutination |
| 200 × 2 = 400 | 1 drop negative, 2 drops positive agglutination |

As seen from the above data, as the amount of IgG present in the Example decreased, the amount of serum sample required for agglutination increased. It was necessary to increase the dilution of the serum sample because the increase in latex particle size produced a decrease in the surface area of the latex particles.

EXAMPLE V

A 10 percent aqueous solution of polystyrene latex particles, having a particle size of 0.807 microns was diluted 1:5 with the buffer of Example I to a final concentration of about 2 percent (w/v).

For each test, 5 μl of foal serum was added to 1080 ml of the above buffer and mixed well to a final concentration of 0.01 part serum to 2160 parts buffer. One drop of the diluted latex was mixed on a slide with 1 or 3 drops of the diluted serum as described in Example I. Test results obtained are summarized below.

TABLE VI

| mg/dl IgG (RID) | Amount of Serum Added |
|---|---|
| 900 × 2 = 1800 | 1 drop positive agglutination |
| 370 × 2 = 740 | 1 drop negative agglutination, 3 drops positive agglutination |
| 200 × 2 = 400 | 3 drops negative agglutination |

As seen from the above data, as the amount of IgG present in the serum sample decreased, the amount of serum sample required for agglutination increased. The above data illustrates further the effect shown in Example IV; an increase in latex particle size produced a decrease in the surface area of the latex particles, requiring a further increase in the dilution of the serum sample.

EXAMPLE VI

Ten grams of sodium chloride were added to 1 liter of the buffer of Example I to produce a N,N-bis-2-hydroxyethylglycine-saline buffer. A 10 percent aqueous solution of polystyrene butadiene latex particles, having a particle size of 0.109 microns was diluted 1:15 in this buffer to a final concentration of about 0.67 percent (w/v).

For each test, 5 μl of foal serum was added to 6 ml of the above buffer and mixed well. One drop of the diluted latex mixture was mixed on a slide with 1, 2 or 3 drops of the diluted serum as described in Example I. Test results obtained are summarized below.

TABLE VII

| mg/dl IgG (RID) | Amount of Serum Added |
|---|---|
| 750 × 2 = 1500 | 1 drop positive agglutination |
| 500 × 2 = 1000 | 1 drop positive agglutination |
| 375 × 2 = 750 | 1 drop positive agglutination |
| 300 × 2 = 600 | 1 drop positive agglutination |
| 250 × 2 = 500 | 1 drop negative 2 drops positive agglutination |
| 166 × 2 = 332 | 1 and 2 drops negative, 3 drops positive agglutination |

As seen from the above data, as the amount of IgG present in the serum sample decreased, the amount of serum sample required for agglutination increased. In addition, these results also demonstrate the change achieved by selection of the buffer. The addition of saline to the buffer causes the 0.109 micron latex particles to function in a manner more similar to the 0.22 micron latex particles of Example II than to the 0.109 micron latex particles of Example III.

Foal serum samples were mixed to produce a series having 3000 mg/dl and 1500 mg/dl IgG, as determined by RID testing, and used as described in the following example.

EXAMPLE VII

A 10 percent aqueous solution of polystyrene latex particles, having a particle size of 0.22 microns was diluted 1:5 with a glycine buffer (0.1M, pH 8.2) to a final concentration of about 2 percent (w/v).

For each test, 5 μl of foal serum was added to 6 ml of the above glycine buffer and mixed well. One drop of the diluted latex was mixed on a slide with 1, 2 or 3 drops of the diluted serum as described in Example I. Test results obtained are summarized below.

TABLE VIII

| mg/dl IgG (RID) | Amount of Serum Added |
|---|---|
| 3000 × 2 = 6000 | 1 and 2 drops negative, 3 drops positive agglutination |
| 1500 × 2 = 3000 | 1, 2, and 3 drops negative agglutination |

Again, as the amount of IgG present in the serum sample decreased, the amount of serum sample required for agglutiantion increased. The presence of glycine in place of the buffer of the previous example requires the presence of a large amount of IgG to produce agglutination.

EXAMPLE VIII

A 10 percent aqueous solution of polystyrene latex particles, having a particle size of 0.22 microns was diluted 1:5 with a glycine-saline buffer (0.1M, pH 8.2, 10 grams sodium chloride per L) to a final concentration of about 2 percent (w/v).

For each test, 5 µl of foal serum was added to 6 ml of the glycine-saline buffer and mixed well. One drop of the diluted latex was mixed on a slide with 1, 2 or 3 drops of the diluted serum as described in Example I. Test results obtained are summarized below.

TABLE IX

| mg/dl IgG (RID) | Amount of Serum Added |
| --- | --- |
| 750 × 2 = 1500 | 1 drop positive agglutination |
| 500 × 2 = 1000 | 1 drop positive agglutination |
| 375 × 2 = 750 | 1 drop positive agglutination |
| 300 × 2 = 600 | 1 drop positive agglutination |
| 250 × 2 = 500 | 1 drop negative, 2 drops positive agglutination |
| 166 × 2 = 332 | 1 and 2 drops negative, 3 drops positive agglutination |

Again, as the amount of IgG present in the serum sample decreased, the amount of serum sample required for agglutination increased. The addition of saline to the glycine buffer of Example VII greatly increased the IgG test sensitivity. Where the glycine alone as a buffer required large amounts of IgG for agglutination, the above glycine-salt buffer had a sensitivity similar to that shown in Example II (N,N-bis-2-hydroxyethylglycine buffer).

EXAMPLE IX

A 10 percent solution of polystyrene latex particles, having a particle size of 0.22 microns was diluted 1:5 with a borate-saline buffer (0.125M, pH 8.4, 8.5 gms sodium chloride/L) to a final concentration of about 2 percent (w/v).

The borate-saline buffer was prepared by mixing 50 cc of 0.1M boric acid and 5.9 ml of 0.1N NaOH made up to 100 cc with water and the pH adjusted to about 8.2; 0.85 gm of NaCl was added to each 100 ml of buffer.

For each test, 5 µl of foal serum was added to 6 ml of the borate-saline buffer and mixed well. One drop of the diluted latex was mixed on a slide with 1, 2 or 3 drops of the diluted serum as described in Example I. Test results were essentially the same as for the glycine-saline buffer of Example VIII.

EXAMPLE X

A 10 percent aqueous solution of polystyrenebutadiene latex particles, having a particle size of 0.109 microns was diluted 1:5 with the buffer of Example I to a final concentration of about 2 percent.

For each test, foal serum samples were prepared as described in Example I. Five µl of foal serum was added to 10 ml of the above buffer and mixed well. One drop of the diluted serum was added to 1 drop of the diluted latex as described in Example I. Test results obtained are summarized below.

TABLE X

| mg/dl IgG (RID) | Amount of Serum Added |
| --- | --- |
| 900 × 2 = 1800 | 4 drops positive agglutination |
| 370 × 2 = 740 | 7 drops positive agglutination |
| 200 × 2 = 400 | 9 drops positive agglutination |

The agglutination could be reversed by adding another drop of diluted latex and then agglutinated again by more diluted serum. This reversibility of agglutination demonstrates that the end-point can be carefully "pin-pointed".

EXAMPLE XI

The procedure of Example I and Example II was repeated using neonatal calf serum in place of foal serum. Test results indicated that as the amount of IgG present in the serum sample decreased, the amount of serum sample required for agglutination increased. Test results indicated that the method of the present invention can be used to measure agglutination and determine the amount of IgG present in the calf serum sample.

EXAMPLE XII

The procedure of Example I can be repeated with colostrum in place of serum, to determine the suitability of colostrum from a parturient mare or cow to transfer immunoglobulin to a neonatal calf or foal.

Useful colostrum will have an IgG level of approximately 1,000 mg/dl or above. In order to bring the colostrum sample into a range which approximates the serum range of Example I, the colostrum is diluted 1:5 with a suitable buffer to produce a range of about 200 mg/dl.

A 10 percent (w/v) solution of polystyrene particles, having a particle size of 0.22 microns is diluted 1:5 (v/v) basis with N,N-bis-2-hydroxyethylglycine buffer (0.2M, pH 8.5) to a final concentration of about 2 percent (w/v).

For each test, a 5 µl sample of the diluted colostrum is added to 8 ml of the above buffer and mixed well to a final concentration of 0.01 part diluted colostrum to 16 parts buffer (v/v). This dilution is then used for titration of 2 drops latex as in Example I.

EXAMPLE XIII

This example compares the results of the agglutination determination of IgG in the serum and whole blood samples from the same newborn foals. The Control Procedure described earlier (RID) was used to determine the serum IgG level. Since the concentration of IgG in a whole blood sample is expected to be about half that of serum from the same animal, the dilution of the blood samples with buffer is only half that used with the serum samples in order to achieve a similar agglutination. Two 5-microliter pipettes full of whole blood were mixed with 8 ml N,N-bis-2-hydroxyethylglycine buffer (0.2M, pH 8.5) to a final dilution of 0.01:8. One 5-microliter pipette full of serum was mixed with 8 ml buffer to a final dilution of 0.01:16. A 10 percent (w/v) solution of polystyrene latex particles having a particle size of 0.22 microns was diluted 1:15 (v/v) with the same buffer to a final concentration of 0.67 percent (w/v).

To three rings on a slide were added respectively 2 drops, 3 drops, and 4 drops of diluted blood (0.01:8). Two drops (0.04 ml./drop) of the latex particle mixture were added to each ring and mixed. The slide was gently rocked and rotated back and forth; the mixture was observed for agglutination. Agglutination was read after 1 minute and the pattern was recorded. This procedure was then repeated using diluted serum (0.01:16). The results are shown in Table XI.

TABLE XI

COMPARISON OF LATEX AGGLUTINATION PATTERNS FOR SERUM AND WHOLE BLOOD

| Foal No. | RID mg/dl IgG (Serum) | LATEX TEST RESULTS Serum | | | LATEX TEST RESULTS Blood | | |
|---|---|---|---|---|---|---|---|
| | | 2 dr | 3 dr | 4 dr | 2 dr | 3 dr | 4 dr |
| 9 | 1500 | + | + | + | + | + | + |
| 13A | 700 | + | + | + | + | + | + |
| 16 | 300 | − | + | + | − | + | + |
| 24 | 265 | − | + | + | − | + | + |
| 31 | 520 | + | + | + | + | + | + |
| 856 | <100 | − | − | − | − | − | − |
| 857 | <100 | − | − | − | − | − | − |
| 863 | 305 | − | + | + | − | + | + |
| 872 | 380 | − | + | + | − | + | + |
| 879 | 500 | + | + | + | + | + | + |
| 884 | 210 | − | + | + | − | + | + |
| 891 | <100 | − | − | − | − | − | − |

It thus appears that the following agglutination patterns can be used to determine the respective quantities of IgG in both serum and whole blood.

| Latex Agglutination Pattern | IgG mg/dl |
|---|---|
| + + + | ≧400 |
| − + + | 200–400 |
| − − + | <200 |
| − − − | <100 |

What is claimed is:

1. A method for determining the amount of IgG present in a neonatal calf or foal or in the colostrum of a cow or dam, which comprises the steps of contacting a body fluid sample from said neonatal or said colostrum with biologically inert latex particles, measuring the amount of agglutination which occurs and determining therefrom the amount of IgG present in said sample, wherein said latex particles, having a particle size from 0.109 to 0.81 microns are diluted with a buffer to a final concentration of from 0.25 to 2.0 percent, weight-/volume basis at a pH of from about 7.5 to 9.0, and wherein said body fluid sample is diluted with a buffer to a range of from 0.01:5 parts to 0.01:2160 parts, v/v basis, at a pH of from about 7.5 to 9.0.

2. A method as claimed in claim 1 wherein the body fluid is blood plasma, blood serum or whole blood.

3. A method as claimed in claim 1 wherein the body fluid is colostrum.

4. A method as claimed in claim 1 wherein the buffer is selected from the group consisting of borate-saline, glycine-saline, and N,N-bis-2-hydroxyethylglycine.

5. A method as claimed in claim 1 wherein the latex particles have a particle size of 0.190 to 0.250 microns and are diluted with buffer to a final concentration of 0.65 to 0.70 percent, weight/volume basis.

6. A method as claimed in claim 1 wherein the body fluid is diluted with buffer in the range of 0.01:8 to 0.01:16.

* * * * *